US012807666B2

(12) United States Patent
Choi et al.

(10) Patent No.: US 12,807,666 B2
(45) Date of Patent: Nov. 24, 2026

(54) TRANSFORMED IMMUNE CELLS INDUCING CHEMOTAXIS TOWARDS HETEROGENEOUS IMMUNE CELLS

(71) Applicant: TSD LIFE SCIENCES CO., LTD., Seoul (KR)

(72) Inventors: Ki Doo Choi, Suwon-si (KR); Dohyun Son, Namyangju-si (KR); Milim Lee, Goyangsi (KR); Sanghyeon Oh, Seoul (KR)

(73) Assignee: TSD LIFE SCIENCES CO., LTD, Seoul (KR)

( * ) Notice: Subject to any disclaimer, the term of this patent is extended or adjusted under 35 U.S.C. 154(b) by 770 days.

(21) Appl. No.: 18/033,484

(22) PCT Filed: Oct. 28, 2021

(86) PCT No.: PCT/KR2021/015290

§ 371 (c)(1),
(2) Date: Apr. 24, 2023

(87) PCT Pub. No.: WO2022/092841

PCT Pub. Date: May 5, 2022

(65) Prior Publication Data

US 2023/0382968 A1 Nov. 30, 2023

(30) Foreign Application Priority Data

Oct. 28, 2020 (KR) ........................ 10-2020-0141039

(51) Int. Cl.

| | |
|---|---|
| ***C07K 14/54*** | (2006.01) |
| ***A61K 40/15*** | (2025.01) |
| ***A61K 40/42*** | (2025.01) |
| ***A61P 35/00*** | (2006.01) |
| ***C07K 14/52*** | (2006.01) |
| ***C12N 5/0783*** | (2010.01) |

(52) U.S. Cl.

CPC .......... *C07K 14/5418* (2013.01); *A61K 40/15* (2025.01); *A61K 40/42* (2025.01); *A61P 35/00* (2018.01); *C07K 14/521* (2013.01); *C12N 5/0636* (2013.01); *C12N 5/0646* (2013.01)

(58) Field of Classification Search

CPC .. C07K 14/5418; C07K 14/521; A61K 40/15; A61K 40/35; C12N 2502/1164

See application file for complete search history.

(56) References Cited

U.S. PATENT DOCUMENTS

| | | | |
|---|---|---|---|
| 11,337,997 | B2 | 5/2022 | Tamada et al. |
| 11,617,765 | B2 | 4/2023 | Tamada et al. |
| 11,931,381 | B2 | 3/2024 | Tamada et al. |
| 2014/0255363 | A1 | 9/2014 | Metelitsa et al. |
| 2019/0099446 | A1 | 4/2019 | Tamada et al. |
| 2020/0323920 | A1 | 10/2020 | Tamada et al. |
| 2020/0352997 | A1 | 11/2020 | Tamada et al. |
| 2022/0273723 | A1 | 9/2022 | Tamada et al. |
| 2022/0401480 | A1 | 12/2022 | Tamada et al. |
| 2024/0139248 | A1 | 5/2024 | Tamada et al. |
| 2024/0226157 | A1 | 7/2024 | Tamada et al. |
| 2024/0269174 | A1 | 8/2024 | Tamada et al. |
| 2024/0307451 | A1 | 9/2024 | Tamada et al. |
| 2024/0317882 | A1 | 9/2024 | Zhang et al. |
| 2024/0350627 | A1 | 10/2024 | Take et al. |

FOREIGN PATENT DOCUMENTS

| | | | |
|---|---|---|---|
| CN | 1629285 | A | 6/2005 |
| CN | 100359004 | C | 1/2008 |
| CN | 108060137 | A | 5/2018 |
| CN | 108949789 | A | 12/2018 |
| CN | 110590960 | A | 12/2019 |
| KR | 10-2019-0051039 | A | 5/2019 |
| WO | 2017/159736 | A1 | 9/2017 |
| WO | 2019/073973 | A1 | 4/2019 |
| WO | 2019/124468 | A1 | 6/2019 |
| WO | 2020/027832 | A1 | 2/2020 |
| WO | 2021/085497 | A1 | 5/2021 |
| WO | 2021/244654 | A1 | 12/2021 |
| WO | 2022/227511 | A1 | 11/2022 |
| WO | 2023/007431 | A1 | 2/2023 |

OTHER PUBLICATIONS

Extended European Search Report dated Oct. 1, 2024 in Application No. 21886835.4.

Communication dated Sep. 16, 2025 in Japanese Application No. 2023-527240.

Duan, et al., "The BCMA-Targeted Fourth-Generation CAR-T Cells Secreting IL-7 and CCL19 for Therapy of Refractory/Recurrent Multiple Myeloma", Frontiers in Immunology, Mar. 2021, vol. 12, Article 609421, pp. 1-11 (11 pages).

Pang, et al., "IL-7 and CCL19-secreting CAR-T cell therapy for tumors with positive glypican-3 or mesothelin", Journal of Hematology & Oncology, 2021, vol. 14, No. 118, pp. 1-6 (6 pages).

Adachi et al., "The novel strategies for CAR-T cell therapy targeting solid cancers", Experimental Medicine, 2020, vol. 38, No. 17, pp. 107-121 (2899-2913) (15 pages).

(Continued)

*Primary Examiner* — Gyan Chandra

(74) *Attorney, Agent, or Firm* — Sughrue Mion, PLLC

(57) ABSTRACT

Immune cells expressing IL-7, CCL19, or a combination thereof, and a composition containing the immune cells, which is useful for preventing or treating cancer or infectious diseases are disclosed. A method for preventing or treating cancer or infectious diseases, which include administering a therapeutically effective amount of single type of immune cells, specifically natural killer cells, is also disclosed. Complementary immune responses between the patient's endogenous T cells and injected natural killer cells exhibit multifaceted and synergistic therapeutic effects. Co-administration of T cells and the immune cells other than T cells, specifically natural killer cells, also significantly improves therapeutic effects by allowing these heterogeneous cell populations to act in a lesion-concentrated manner.

2 Claims, 2 Drawing Sheets

Specification includes a Sequence Listing.

(56) References Cited

OTHER PUBLICATIONS

Ghahri-Saremi, et al., "Genetic Modification of Cytokine Signaling to Enhance Efficacy of Car T Cell Therapy in Solid Tumors", Frontiers in Immunology, Oct. 2021, vol. 12, Article 738456, pp. 1-13 (13 pages).
Keishi Adachi, et al., "IL-7 and CCL19 expression in CAR-T cells improves immune cell infiltration and CAR-T cell survival in the tumor", Nature Biotechnology, Apr. 2018, pp. 346-351, vol. 36, No. 4.
Hong Luo, et al., "Coexpression of IL7 and CCL21 Increases Efficacy of CAR-T Cells in Solid Tumors without Requiring Preconditioned Lymphodepletion", Clinical Cancer Research, Oct. 15, 2020, pp. 5494-5505, vol. 26, No. 20.
International Search Report for PCT/KR2021/015290 dated Feb. 3, 2022 [PCT/ISA/210].

TRANSFORMED IMMUNE CELLS INDUCING CHEMOTAXIS TOWARDS HETEROGENEOUS IMMUNE CELLS

CROSS REFERENCE TO RELATED APPLICATIONS

This application is a National Stage Entry of International Application No. PCT/KR2021/015290 filed Oct. 28, 2021, claiming priority based on Korean Patent Application No. 10-2020-0141039 filed Oct. 28, 2020.

INCORPORATION BY REFERENCE OF SEQUENCE LISTING

The content of the electronically submitted sequence listing, file name: Q286733_Sequence_Listing_As_Filed.txt; size: 3,841 bytes; and date of creation: Apr. 21, 2023 filed herewith, is incorporated herein by reference in its entirety.

TECHNICAL FIELD

The present invention relates to immune cells, specifically those other than T cells, more specifically natural killer cells, that express specific chemotactic factors for the migration of T cells to the lesion site.

BACKGROUND OF THE INVENTION

Cancer is basically a disease associated with abnormal growth regulation of tissues, and cancer cells grow and proliferate excessively compared to normal cells and characteristically invade adjacent tissues or metastasize to distant tissues. Anti-cancer treatment inhibits the expression of genes necessary for cancer cell survival, such as oncogenes, telomerase, growth factor receptors, or signaling molecules, or induces cell death through physical removal of cancer tissue, irradiation, or administration of anticancer drugs. However, since normal cells may be also damaged alongside cancer cells during this practice, immune cell therapy that specifically remove tumor tissue are receiving attention. In particular, anti-cancer therapy that remove tumor tissue by activating the patient's bodily immune response using immune cells such as dendritic cells, natural killer cells and T cells have been intensively studied in the past decades.

Natural killer cells (NK cells) are lymphoid cells that account for about 15% of peripheral blood lymphocytes and play a crucial role in the innate immune response. In particular, they remove tumor cells by activating dendritic cells and inducing cytotoxic T lymphocytes (CTLs) to specifically react to the tumor. Natural killer cells directly kill malignant tumors including sarcomas, myelomas, lymphomas and leukemia, and its therapeutic effect was confirmed by administration of in vitro—activated NK cells to patients with blood cancer, such as leukemia, after bone marrow transplantation (*Blood Cells Molecules & Disease,* 33: p 261-266, 2004). However, since most natural killer cells are in an inactive state in the body of a normal person, studies have been focused on in vitro activation of NK cells isolated from blood for increased treatment efficiency.

On the other hand, T cells, which constitute another axis among immune cells, are lymphocytes that are generated in the bone marrow and matured in the thymus. They have memory functions in the immune system and provide information to B cells to induce antibody production. After undergoing an immune tolerance test in the thymus, T cells differentiate into 4 types: cytotoxic T cells, helper T cells, regulatory T cells and memory T cells. Cytotoxic T cells, which are CD8+, bind to type I MHC to identify cancer cells or infected cells, and mainly target lesional cells like natural killer cells.

Although therapeutic effects can be maximized when natural killer cells and cytotoxic T cells are administered in combination, the development of novel therapies that can overcome the inefficiency of injecting two cells with each therapeutically effective amount is required.

Throughout this application, various publications and patents are referred and citations are provided in parentheses. The disclosures of these publications and patents in their entities are hereby incorporated by references into this application in order to fully describe this invention and the state of the art to which this invention pertains.

DISCLOSURE OF THE INVENTION

Technical Problem

The present inventors have made intensive studies to develop an excellent cell therapy enabling effective removal of diseased cells or tissues through a complex immune response by a combination of heterogeneous immune cells. As results, the present inventors have discovered that when immune cells, specifically immune cells other than T cells, and more specifically natural killer cells, that express IL-7, CCL19 or a combination thereof, are injected into a subject, endogenous T cells proliferated and homed by the IL-7 and CCL19, along with injected natural killer cells, simultaneously act on the lesion site and thus induce a multifaceted and synergistic immune response.

Accordingly, it is an object of this invention to provide an immune cell expressing IL-7, CCL19 or a combination thereof; and a composition for preventing or treating cancer or infectious diseases comprising the same an active ingredient.

It is another object of this invention to provide a composition for inducing the proliferation or homing of heterogeneous immune cells comprising nucleic acid molecules encoding IL-7, CCL19 or a combination thereof, as an active ingredient.

Other objectives and advantages of the present invention will become apparent from the following detailed description together with the appended claims and drawings.

Technical Solution

In one aspect of the present invention, there is provided an immune cell expressing a nucleic acid molecule encoding IL-7 (interleukin-7) or a functional portion thereof, a nucleic acid molecule encoding CCL19 (C—C Motif Chemokine Ligand 19) or a functional portion thereof, or a combination thereof.

The present inventors have made intensive studies to develop an excellent cell therapy enabling effective removal of diseased cells or tissues through a complex immune response by a combination of heterogeneous immune cells. As results, the present inventors have discovered that when immune cells, specifically immune cells other than T cells, and more specifically natural killer cells, that express IL-7, CCL19 or a combination thereof, are injected into a subject, endogenous T cells proliferated and homed by the IL-7 and CCL19, along with injected natural killer cells, simultaneously act on the lesion site and thus induce a multifaceted and synergistic immune response.

The term "immune cell" as used herein refers to any cell involved in the initiation or promotion of an immune response, and more particularly, an immune effector cells. Immune cells include, for example, T cells, B cells, natural killer (NK) cells, natural killer T (NKT) cells, mast cells and dendritic cells, but are not limited thereto. More concretely, the immune cell is an immune cell other than T cell, and most concretely, a natural killer cell.

The term "T cell" as used herein is a group of cells in the same scope as those understood in the art and includes CD8+ or CD4+ T cells that directly lyses target cells or provides an effector function or helper function which causes the death of target cells, but is not limited thereto and may include any cell classified as "T cell" in the art to which the present invention pertains.

The term "functional portion" as used herein refers to an equivalent fragment of full-length protein form where certain amino acid residues are deleted, which maintains original biological activity and function of the full-length protein.

The term "nucleic acid molecule" as used herein has comprehensive meaning including DNA (gDNA and cDNA) and RNA molecule. A nucleotide, which is a basic construct unit of nucleic acid molecule, includes nucleotide analogues with modified sugar or base, as well as natural-occurring nucleotides (Scheit, *Nucleotide Analogs*, John Wiley, New York (1980); Uhlman and Peyman, *Chemical Reviews,* 90:543-584(1990)).

It would be obvious to the skilled artisan that the nucleotide sequences used in this invention are not limited to those listed in the appended Sequence Listings.

For nucleotides, the variations may be purely genetic, i.e., ones that do not result in changes in the protein product. This includes nucleic acids that contain functionally equivalent codons, or codons that encode the same amino acid, such as six codons for arginine or serine, or codons that encode biologically equivalent amino acids. Considering biologically equivalent variations described hereinabove, the nucleic acid molecule of this invention may encompass sequences having substantial identity to them. Sequences having the substantial identity show at least 80%, concretely at least 85%, more concretely at least 90%, and most concretely at least 95% similarity to the nucleic acid molecule of this invention, as measured using one of the sequence comparison algorithms well-known in the art.

The term "express" as used herein includes artificial expression of an exogenous gene that is not naturally expressed by the immune cell of the present invention through a gene carrier, natural expression of an endogenous gene through an endogenous expression system, and overexpression of endogenous gene by increasing expression of endogenous genes by a gene carrier. Therefore, the immune cell of the present invention includes a cell endogenously expressing IL-7 and CCL19, a cell endogenously expressing IL-7 and artificially expressing CCL19, a cell endogenously expressing CCL19 and artificially expressing IL-7, and a cell artificially expressing IL-7 and CCL19.

The term "to express" as used herein refers to being artificially replicated as an extrachromosomal factor or by chromosomal integration in a target cell via a gene delivery system to cause the target cell to express a foreign gene or overexpress an endogenous gene. Accordingly, "express" in the term "to express" may be used interchangeably with "transformation", "transfection", or "transduction".

The "gene delivery system" as used herein refers to any means of delivering a gene into a cell. The gene delivery has the same meaning as intracellular transduction of genes. At the tissue level, the term gene delivery has the same meaning as the spread of a gene.

Accordingly, the gene delivery system of the present invention can be described as a gene penetration system or a gene spread system.

The nucleotide sequences of the IL-7 and CCL19 gene may be applied to all gene delivery systems used for conventional gene transfers, such as plasmid, adenovirus, adeno-associated virus, retrovirus, lentivirus, herpes simplex virus, vaccinia virus, liposom or niosome.

Where the gene delivery system of the present invention is a naked recombinant DNA molecule or a plasmid, the gene can be introduced into cells by microinjection (Capecchi, M. R., *Cell,* 22:479(1980)), calcium phosphate precipitation (Graham, F. L. et al., *Virology,* 52:456(1973)), electroporation (Tur-Kaspa et al., *Mol. Cell Biol.,* 6:716-718 (1986)), liposome-mediated transfection (*Biochim. Biophys. Acta,* 721:185-190(1982)), DEAE-dextran treatment (Gopal, *Mol. Cell Biol.,* 5:1188-1190(1985)) and gene bombardment (Yang et al., *Proc. Natl. Acad. Sci.,* 87:9568-9572 (1990)), and concretely, electroporation may be used.

According to a concrete embodiment, the IL-7 comprises the amino acid sequences with at least 85% sequence similarity, more concretely at least 90% similarity, and most concretely at least 95% sequence similarity with the amino acid sequence of SEQ ID NO:1.

According to a concrete embodiment, the CCL19 comprises amino acid sequences with at least 85% or more similarity, more concretely at least 90% or more sequence similarity, and most concretely at least 95% or more sequence similarity with the amino acid sequence of SEQ ID NO:2.

According to a concrete embodiment, nucleic acid molecules encoding IL-7 or a functional portion thereof comprises the nucleotide sequence of SEQ ID NO:3.

According to a concrete embodiment of the present invention, nucleic acid molecules encoding CCL19 or a functional portion thereof comprises the nucleotide sequence of SEQ ID NO:4.

According to the present invention, SEQ ID NO:3 and SEQ ID NO:4 are codon optimized nucleotide sequences of IL-7 and CCL19, respectively, for effective expression in natural killer cells.

In another aspect of this invention, there is provided a composition for the prevention or treatment of cancer or infectious diseases comprising the aforementioned immune cells of the present invention as an active ingredient.

In case the immune cells of the present invention are applied as cell therapy, it may be utilized for the treatment of various tumors and infectious diseases. The immune cells of the present invention, in particular natural killer cells, can be applied to all types of tumors including solid cancer and blood cancer. Such cancer may include, but not limited thereto, gastric cancer, liver cancer, lung cancer, colorectal cancer, breast cancer, prostate cancer, ovarian cancer, pancreatic cancer, cervical cancer, thyroid cancer, laryngeal cancer, acute myelogenous leukemia, brain tumor, neuroblastoma, retinoblastoma, head and neck cancer, salivary gland cancer and lymphoma. Infectious diseases that may be prevented or treated by the immune cells of the present invention, particularly natural killer cells, may be diseases caused by viral or pathogenic infections, which include all diseases that can be infected through respiratory, blood, skin contact, and the like. Such infectious disease include, but are not limited to, hepatitis B and C, human papilloma virus (HPV) infection, cytomegalovirus infection, viral respiratory disease and influenza.

The term "prevention" as used herein refers to suppressing the outbreak of illness or disease in a subject who has not been diagnosed with the illness or disease, but is likely to suffer from the illness or disease.

The "treatment" as used herein refers to (a) inhibition of the development of a disease, illness or symptoms, (b) alleviation of the disease, illness or symptoms, or (c) elimination of the disease, illness or symptoms. When the immune cells of the present invention are administered to a subject, a complex immune response is generated by natural killer cells and endogenous T cells or exogenously injected autologous or allogeneic T cells recruited to the lesion site by the natural killer cells, which serves to inhibit, eliminate or alleviate the development of symptoms caused by tumors or infectious diseases by inducing the killing of cancer cells, infected cells, or pathogens. Therefore, the composition of the present invention may itself be a cell therapy composition for diseases, or may be applied as a therapeutic adjuvant for the disease by being administered together with other active ingredients, such as therapeutic T cells or other known anticancer agents. Accordingly, the term "treatment" or "therapeutic agent" in the present specification includes the meaning of "therapeutic aid" or "therapeutic adjuvant".

The term "administration" or "to administer" as used herein refers to the direct administration of a therapeutically effective amount of the composition of the present invention to a subject so that the same amount is formed in the body of the subject.

The terms "therapeutically effective amount" as used herein refer to the content of the composition of the present invention that is sufficient to provide a therapeutic or prophylactic effect to a subject to whom the composition is to be administered, and thus include the meaning of a "prophylactically effective amount".

The term "subject" as used herein includes, without limitation, humans, mice, rats, guinea pigs, dogs, cats, horses, cows, pigs, monkeys, chimpanzees, baboons or rhesus monkeys. Concretely, the subject of the present invention is humans.

In another aspect of this invention, there is provided a composition for inducing proliferation or homing of a heterogeneous immune cell comprising a nucleic acid molecule encoding IL-7 (interleukin-7) or a functional portion thereof, a nucleic acid molecule encoding CCL19 (C—C Motif Chemokine Ligand 19) or a functional portion thereof, or a combination thereof, as an active ingredient.

Since the nucleic acid molecules used in the present invention have already been described in detail above, descriptions thereof are omitted to avoid excessive redundancy.

The term "heterogeneous immune cells" used herein refers to immune cells of a different type from the target cell into which the nucleic acid molecule of the present invention is introduced. Concretely, the heterogeneous immune cells are T cells or dendritic cells. According to the present invention, a large amount of endogenous T cells can be migrated to the lesion by injecting immune cells simultaneously expressing IL-7 and CCL19, concretely immune cells other than T cells, and most concretely natural killer cells, into the subject to induce proliferation and chemotaxis of T cells. The term "chemotaxis" refers to the positive (towards a stimulus) or negative (away from a stimulus) migration of cells which is induced by chemical stimuli, and more concretely refer to positive migration. According to the present invention, T cells are proliferated and differentiated by IL-7 and activated by CCL19, a corresponding chemotactic factor, and then move toward natural killer cells expressing IL-7 and CCL19. This results in formation of heterogeneous cell population composed of two types of complementary immune cells, i.e. T cells and natural killer cells, around the lesion site. Accordingly, the composition of the present invention may act as a therapeutic adjuvant that provides the effect for co-administration of different cell populations only by a therapeutically effective amount of a single cell type.

According to a concrete embodiment, the nucleic acid molecules can be included in the composition by being inserted together into single gene delivery system or each separately into two different gene delivery systems.

According to another aspect of the present invention, the present invention provides a method for preventing or treating cancer or infectious diseases comprising administering the aforementioned immune cells of the present invention to a subject. Since the immune cells used in the present invention and the cancer and infectious diseases that can be prevented or treated thereby have already been described above in detail, descriptions thereof are omitted to avoid excessive redundancy.

According to another aspect of the present invention, the present invention provides a method for inducing a proliferation or homing of a heterogeneous immune cell comprising introducing a nucleic acid molecule encoding IL-7 (interleukin-7) or a functional portion thereof, a nucleic acid molecule encoding CCL19 (C—C Motif Chemokine Ligand 19) or a functional portion thereof, or a combination thereof, into an immune cell. Since the nucleic acid molecules and heterologous immune cells used in the present invention have already been described above in detail, descriptions thereof are omitted to avoid excessive redundancy.

Effects of the Invention

The features and advantages of the present invention are summarized as follows:

(a) The present invention provides immune cells expressing IL-7, CCL19 or a combination thereof, and a composition for the preventing or treating cancer or infectious diseases comprising the same as an active ingredient.

(b) The present invention may achieve a multifaceted and synergistic therapeutic effect through administering a therapeutically effective amount of single type of immune cells, specifically natural killer cells, due to the complementary immune responses between the patient's endogenous T cells and injected natural killer cells (c) According to the present invention, co-administration of T cells and the immune cells other than T cells, specifically natural killer cells, also significantly improve therapeutic effects by allowing these heterogeneous cell populations to act in a lesion-concentrated manner.

Hereinafter, the present invention will be described in further detail by examples. It would be obvious to those skilled in the art that these examples are intended to be more concretely illustrative and the scope of the present invention as set forth in the appended claims is not limited to or by the examples.

EXAMPLES

Example 1: Construction of IL-7 and CCL19 Expression Vectors

Expression vectors were constructed to prepare human NK cells expressing IL-7 and CCL19. A pEF1α-IRES bicistronic mammalian expression vector (Takara, CAT #631970) under the control of human elongation factor 1 alpha (EF1α) promoter was used as an expression vector.

Figure 1:
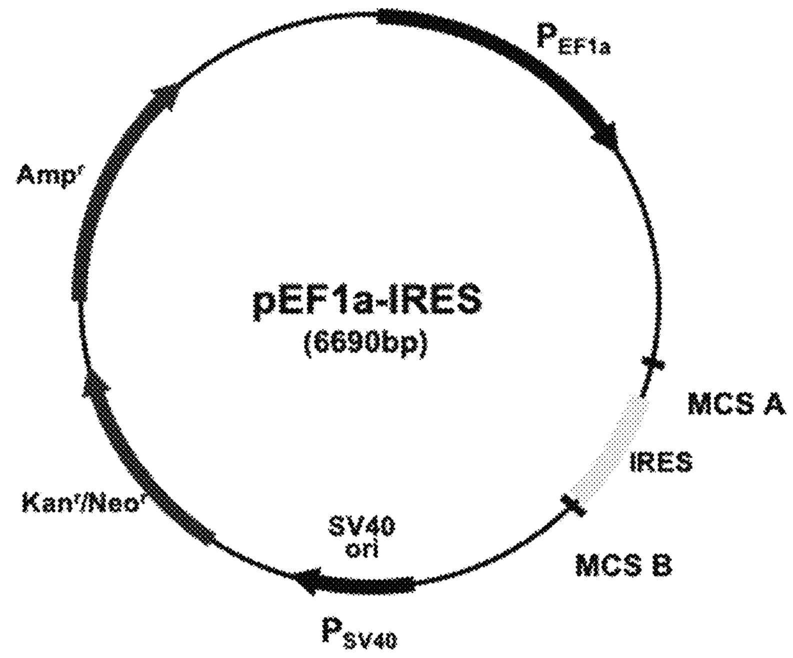
FIG. 1 represents a schematic diagram showing the structure of the pEF1-IRES empty vector used as a negative control vector.
Figure 2:
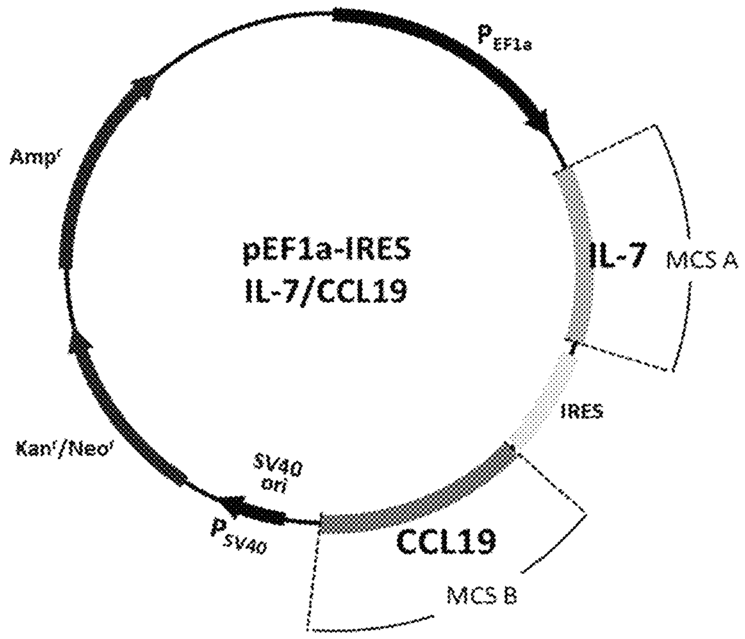
FIG. 2 represents a schematic diagram showing the structure of the pEF1-IRES vector into which IL-7 and CCL19 genes are inserted.
Figure 3:
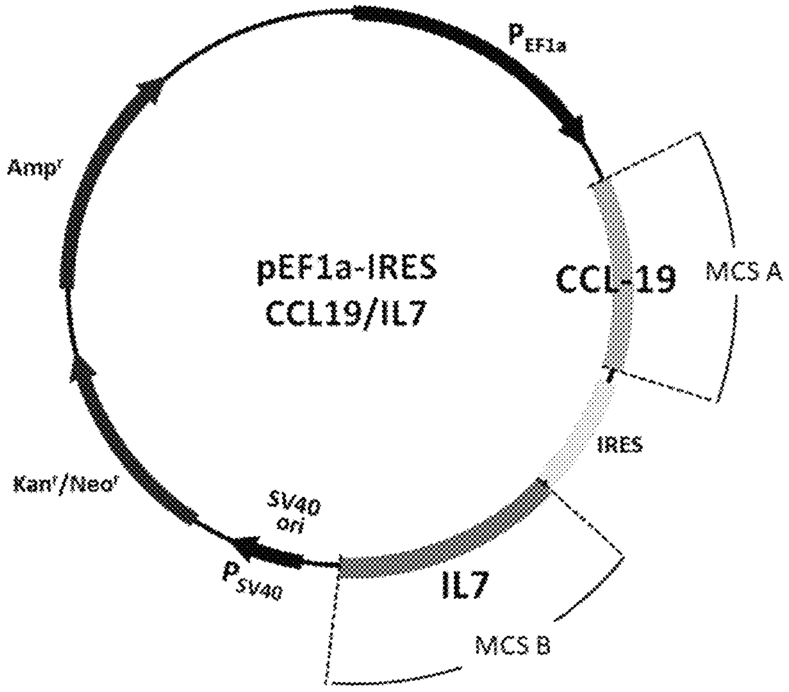
FIG. 3 represents a schematic diagram showing the structure of the pEF1-IRES vector into which CCL19 and IL-7 genes are inserted.

The ORF sequences of IL-7 and/or CCL19 genes to be inserted into the vector were codon-optimized (SEQ ID NO:3 and SEQ ID NO:4, respectively) and synthesized. IL-7 or CCL19 was cloned into the multicloning site A (MCS A) of the pEF1α-IRES vector, and CCL19 or IL-7 was cloned into MCS B. Here, an internal ribosome entry site (IRES) was positioned between the two MCSs in the pEF1α-IRES so that the two genes could be co-expressed. The structure of the empty vector, the negative control, is shown in FIG. 1, the structure of the IL-7/CCL19 expression vector is shown in FIG. 2, and the structure of the CCL19/IL-7 expression vector is shown in FIG. 3, respectively.

Example 2: Confirmation of the Expression of IL-7 and CCL19

The NK92 cell line was purchased from ATCC (CAT #CRL-2407), and cultured in α-MEM (Alpha Minimum Essential Medium) containing 12.5% horse serum (Sigma, CAT #H1270), 12.5% fetal bovine serum (FBS, Gibco, CAT #10099141), and interleukin-2 (IL-2, Peprotech, CAT #200-02). In order to prepare a NK92 cell line expressing IL-7 and CCL19 (hereinafter, "transformed NK92 cell line"), electroporation was performed at a density of $1\times10^6$ NK92 cells/0.1 mL.

The electroporation was performed by Neon™ Transfection System (ThermoFisher, CAT #MPK5000) was used under the following conditions: 1800-1850 v voltage, 10 ms pulse length, 1 time, and 10-20 μg DNA (negative control vector, IL-7/CCL19 expression vector, or CCL19/IL-7 expression vector prepared in Example 1). After culturing for 1 day in 2 mL of RPM11640 medium (Gibco #11875168) containing 10% FBS, the expression level of IL-7 or CCL19 was measured or a transwell assay were performed.

In order to measure the expression level of IL-7 and CCL19 in the transformed NK92 cell line, the culture medium was collected in a 6-well plate. After centrifugation at 800×g for 5 minutes, the supernatant was separated. 0.1 mL per well of the supernatant was appropriately diluted and used for IL-7 or CCL19 enzyme linked immunosorbent assay (ELISA; IL-7, Komabiotech, CAT #k0331215; CCL19, Abcam, CAT #ab100601) to measure the expression level of IL-7 or CCL19.

The ELISA for IL-7 and CCL19 was performed according to the standard testing methods of each manufacturer. The final values measured at a wavelength of 450 nm are shown in Table 1.

TABLE 1

Amount of IL-7 and CCL19 secretion in transformed cells

| Cell | Gene | IL-7 (pg/mL) | CCL19 (pg/mL) |
|---|---|---|---|
| NK92 | Empty vector | N.D | 4.2 |
| | IL-7/CCL19 | 1,656 | 242 |
| | CCL19/IL-7 | 157 | 368 |

*N.D: Not Detected

The results of Table 1 indicate that the IL-7/CCL19 NK92 cell line and the CCL19/IL-7 NK92 cell line secreted IL-7 and CCL19, while IL-7 and CCL19 were not detected or were detected at insignificant levels in the negative control cells injected with the empty vector.

Example 3: Analysis of T Cell Chemotaxis and Proliferation Induced by IL-7 and CCL19 Expressing NK Cells To confirm the effect of the secretion of IL-7 and CCL19 by NK cells on T cell chemotaxis, a 12-well transwell (Corning, CAT #CLS3421) was used. 5 μm polycarbonate was used as the chamber filter.

Comparison of IL-7/CCL19 NK92 Cells and Negative Controls Using HuT78 T Cell Line $1\times10^7$ cells of HuT78 (ATT, CAT #TIB-161), the T cells, were cultured for 24 hours in IMDM (Gibco, CAT #12440053) medium containing 1% PS without FBS. Thereafter, 100 μl of HuT78 cells at a density of $5\times10^6$ cells/mL were dispensed into the upper chamber using the same medium as above, and the culture solution cultured for 2-3 days in the IL-7/CCL19 NK92 cell line prepared in Example 2 was dispensed in the lower chamber.

After culturing for 1 day in an incubator at 37 °C and 5% $CO_2$, the upper chamber was removed and further cultured for 3 days. To measure the number of cells in the lower chamber, 400 μl of medium per well was centrifuged at 800×g for 5 minutes to remove the supernatant and obtain a concentrated sample. 10 μl of Trypan blue was mixed with 10 μl of the concentrated sample at a 1:1 ratio and measured with Countess™ II (Invitrogen, CAT #AMQAX1000). The results were converted into the total number of viable cells in 400 μl as shown in Table 2.

TABLE 2

Chemotaxis of the HuT78 T cell line by transformed NK cells

| Experimental Group | Number of cells in the lower chamber (mean ± standard deviation) |
|---|---|
| Negative control cells | 3,836 ± 276 |
| IL-7/CCL19 NK92 cells | 11,989 ± 887 |

Comparison of IL-7/CCL19 NK92 Cells, CCL19/IL-7 NK92 Cells and Negative Control Using PBMC-Derived T Cells To evaluate the chemotaxis of peripheral blood mononuclear cells (PBMC)-derived T cells, T cells were isolated from PBMC using the EasySep™ Human T Cell Isolation Kit (STEMCELL #17951). After diluting the T cells at a concentration of $2\times10^6$ cells/mL with RPM11640 medium containing 2% FBS, 100 μl was dispensed into the upper chamber. In the lower chamber, the culture solution cultured for 1 day in IL-7/CCL19 and CCL19/IL-7 transformed NK92 cell lines prepared in Example 2 was dispensed.

After culturing for 1 day in an incubator at 37 °C and 5% $CO_2$, the upper chamber was removed and further cultured for 3 days. To measure the number of cells in the lower chamber, 500 μl of medium per well was centrifuged at 800×g for 5 minutes to remove the supernatant and obtain a concentrated sample. 10 μl of Trypan blue was mixed with 10 μl of the concentrated sample at a 1:1 ratio and measured with Countess™ II. The results were converted into the total cell numbers as shown in Table 3.

TABLE 3

PBMC-derived T cell chemotaxis by transformed NK92 cell line

| T cell type | Experimental group (n = 2) | Number of T cells migrating to lower chamber (mean ± standard deviation, $10^4$ cells) |
|---|---|---|
| PBMC-derived T cells | Negative control NK92 cells | 1.89 ± 0.75 |
| | IL-7/CCL19 NK92 cells | 9.35 ± 0.53 |
| | CCL19/IL-7 NK92 cells | 6.46 ± 0.16 |

As shown in Tables 2 and 3, the number of T cells that migrated to the lower chamber was significantly higher in the IL-7/CCL19 and CCL19/IL-7 NK92 cell line group compared to the negative control empty vector-introduced NK92 cell line. This indicates that the NK92 cell transformed with IL-7 and CCL19 induced chemotaxis of T cells and proliferation of migrated T cells.

Example 4: Measurement of Cancer Cell Killing and Secretion of the Related Factors by Transformed NK92 Cell Lines and T Cells Migrated Thereby After HepG2 liver cancer cell line (ATCC #HB-8065) was diluted in RPM11640 medium containing 10% FBS to a concentration of $2\times10^5$ cells/mL, 0.1 mL was dispensed into each well of a 96-well plate and cultured for 1 day. T cell migration was induced for 1 day by transferring 0.5 mL RPM11640 medium containing the transformed NK92 cell line cultured for 1 day by electroporation in the same manner as in Example 2 to the lower chamber of the transwell in the same manner as in Example 3. $2\times10^5$ cells/0.1 mL of T cells isolated from PBMC were transferred to the upper chamber. Here, $1\times10^5$ CD3/CD28 Dynabeads and 100 U IL-2 were added to the lower chamber to activate the migrating T cells. After culturing for 1 day, the upper chamber was removed and transferred 0.1 mL per well to the 96-well plate in which the HepG2 liver cancer cell line was being cultured. After culturing for 3 more days and washing three times using PBS (phosphate buffer saline), the medium was replaced with 0.1 mL of 10% FBS-RPM11640 medium containing 1% of CCK-8 and further cultured for 2 hours. In order to evaluate the cell viability of the HepG2 liver cancer cell line, absorbance was measured at 450 nm and the degree of cell viability was calculated using [Equation 1], as shown in Table 4.

[Equation 1]

$$HepG2 \text{ cell line viability} = 100\times\frac{(\text{Test group absorbance value} - RPMI1640 \text{ medium absorbance value})}{(\text{Normal group absorbance value} - RPMI1640 \text{ medium absorbance value})}$$

In addition, the secretion of granzyme-B (Grz-B), interferon-γ (IFN-γ), and tumor necrosis factor-α (TNF-α) from activated T cells and activated NK cells was measured using the medium collected from the cell viability measurement above, via the enzyme-linked immunosorbent assay (ELISA; GrzB, abcam #ab235635; IFN-γ, komabiotech #K0331121; TNF-α, komabiotech #K0331131), of which the results are shown in Table 5. Each value in Table 4 and 5 was expressed as mean±standard deviation.

TABLE 4

Cytotoxicity for HepG2 liver cancer cell line

| Cancer cell line | Experimental group (n = 3) | Cell viability |
|---|---|---|
| HepG2 | Medium (Normal group) | 100.0 ± 7.8 |
| | Negative control group (Empty vector NK92) | 83.8 ± 2.1 |
| | IL-7/CCL19 NK92 cells | 33.2 ± 3.3 |
| | CCL19/IL-7 NK92 cells | 52.2 ± 3.5 |

TABLE 5

Secretion Grz-B, IFN-γ and TNF-α

| Cancer cell line | Experimental group (n = 2) | Grz-B (pg/mL) | IFN-γ (pg/mL) | TNF-α (pg/mL) |
|---|---|---|---|---|
| HepG2 | Medium (Normal group) | 592 ± 179 | N.D | N.D |
| | Negative control (Empty vector NK92) | 1,259 ± 81 | 8 ± 1 | N.D |
| | IL-7/CCL19 NK92 cells | 2,573 ± 450 | 320 ± 28 | 195 ± 37 |
| | CCL19/IL-7 NK92 cells | 1,460 ± 466 | 71 ± 3 | 33 ± 10 |

*N.D: Not Detected

As shown in Table 4, significantly higher cell killing activity toward HepG2 was observed in the experimental group of IL-7/CCL19 and CCL19/IL-7 NK92 cell line compared to the empty vector-introduced NK92 cell as a negative control. As shown in Table 5, the factors related to the cytotoxicity for HepG2 cell line also showed higher secretion in the groups of IL-7/CCL19 and CCL19/IL-7 NK92 cell line compared to the negative control group. Accordingly, it was confirmed that both the IL-7/CCL19 NK cell line and the CCL19/IL-7 NK cell line may be applied as an effective anti-cancer treatment.

Having described specific embodiment of the present invention in detail above, it is to be understood that variants and modifications thereof falling within the spirit of the invention may become apparent to those skilled in this art, and the scope of this invention is to be determined by appended claims and their equivalents.

What is claimed is:

1. An immune cell transformed with a nucleic acid molecule encoding IL-7 (interleukin-7) or a functional portion thereof; and a nucleic acid molecule encoding CCL19 (C—C Motif Chemokine Ligand 19) or a functional portion thereof, wherein the immune cell is a natural killer cell.

2. A method for treating cancer or infectious diseases comprising administering the immune cell according to claim 1 to a subject in need thereof.

* * * * *

SEQUENCE LISTING

<160> NUMBER OF SEQ ID NOS: 4

<210> SEQ ID NO 1
<211> LENGTH: 177
<212> TYPE: PRT
<213> ORGANISM: Homo sapiens

<400> SEQUENCE: 1

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 2
<211> LENGTH: 98
<212> TYPE: PRT
<213> ORGANISM: Homo sapiens

<400> SEQUENCE: 2

Met Ala Leu Leu Leu Ala Leu Ser Leu Leu Val Leu Trp Thr Ser Pro
1               5                   10                  15

Ala Pro Thr Leu Ser Gly Thr Asn Asp Ala Glu Asp Cys Cys Leu Ser
            20                  25                  30

Val Thr Gln Lys Pro Ile Pro Gly Tyr Ile Val Arg Asn Phe His Tyr
        35                  40                  45

Leu Leu Ile Lys Asp Gly Cys Arg Val Pro Ala Val Val Phe Thr Thr
    50                  55                  60

Leu Arg Gly Arg Gln Leu Cys Ala Pro Pro Asp Gln Pro Trp Val Glu
65                  70                  75                  80

Arg Ile Ile Gln Arg Leu Gln Arg Thr Ser Ala Lys Met Lys Arg Arg
                85                  90                  95

Ser Ser

<210> SEQ ID NO 3
<211> LENGTH: 534
<212> TYPE: DNA
<213> ORGANISM: Homo sapiens -continued

<400> SEQUENCE: 3
atgttccacg tctctttccg gtacattttc gggctccccc cactgatact ggttcttctg 60
ccagtcgcat catctgattg tgatatagag ggtaaggacg gaaaacaata tgaatctgta 120
ctgatggtgt caatagacca gcttctcgat agcatgaagg aaattggtag taattgtctt 180
aataatgagt tcaacttctt caaacgccac atatgcgacg ccaataaaga gggtatgttc 240
ttgtttcgcg cggctaggaa actcagacaa tttctcaaaa tgaactctac tggtgacttc 300
gacctccacc ttctgaaagt ttccgaagga actaccattc ttctgaattg tacaggtcag 360
gtcaaagggc gcaaaccagc tgctcttgga gaggcccagc caacgaagtc acttgaagaa 420
aataagtctt tgaaggaaca aaagaagctg aatgacctgt gctttctcaa aaggctgttg 480
caggagatta agacctgttg gaacaaaata ctcatgggga ccaaggagca ctga 534

<210> SEQ ID NO 4
<211> LENGTH: 297
<212> TYPE: DNA
<213> ORGANISM: Homo sapiens

<400> SEQUENCE: 4
atggcactgc tcctcgccct gagtctcctg gtactgtgga catcccctgc gcctacgctc 60
tcaggtacaa atgacgccga agattgctgt ctcagtgtaa cccagaagcc cataccgggt 120
tacattgtac ggaacttcca ttatcttctg ataaaagacg gttgccgagt gcctgccgtg 180
gttttcacga cgttgagagg cagacagctg tgcgccccac ccgaccagcc gtgggtcgag 240
cggatcatac aacgcttgca aagaacgtcc gcgaaaatga aaaggcgctc tagctaa 297